United States Patent [19]

Bauman

[11] 4,159,903

[45] Jul. 3, 1979

[54] ENHANCEMENT OF POLYISOPRENE LATEX PRODUCTION

[75] Inventor: Albert J. Bauman, Sierra Madre, Calif.

[73] Assignee: California Institute of Technology, Pasadena, Calif.

[21] Appl. No.: 819,263

[22] Filed: Jul. 27, 1977

[51] Int. Cl.$^2$ .......................... A01N 9/12; A01N 9/22; A01N 9/24; A01N 9/20

[52] U.S. Cl. ............................................. 71/98; 71/86; 71/92; 71/94; 71/106; 71/111; 71/121

[58] Field of Search .................... 71/121, 86, 106, 111, 71/98

[56] References Cited

U.S. PATENT DOCUMENTS

| | | | |
|---|---|---|---|
| 3,544,304 | 12/1970 | Soper | 71/121 X |
| 3,833,350 | 9/1974 | Cooke et al. | 71/121 X |
| 3,898,257 | 8/1975 | Gregory | 71/121 X |
| 3,991,515 | 11/1976 | Drew | 71/121 X |

*Primary Examiner*—Joseph Paul Brust
*Attorney, Agent, or Firm*—Marvin E. Jacobs

[57] ABSTRACT

Production of high molecular weight polyisoprene latex is enhanced by administering to plants, particularly Guayule Plants, an amine containing at least one two-carbon chain substituent and preferably substituted trialkylamine of the general structure:

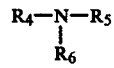

where $R_4$, $R_5$ and $R_6$ are alkyl, preferably ethyl and at least one of $R_4$, $R_5$ and $R_6$ is preferably an electron withdrawing group substituted aryloxy or arylthio ethyl group.

10 Claims, No Drawings

ENHANCEMENT OF POLYISOPRENE LATEX PRODUCTION

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to plant growth regulators, and more particularly, to the enhancement of production of polyisoprene rubber.

2. Description of the Prior Art

Guayule is a desert shrub native to the southwestern United States and northern Mexico that produces polymeric isoprene essentially identical to that made by Hevea rubber trees in Southeast Asia. As recently as 1910 it was the source of half of the natural rubber used in the U.S. Since 1946, however, its use as a source of rubber has been all but abandoned in favor of cheaper Hevea rubber and synthetic rubbers. However, demand for natural rubber is expected to produce shortages of that material as early as 1980 and rubber prices are expected to double by 1985. Natural rubber having lower heat hysteresis is required for many kinds of tires and amounts to about 35% of U.S. rubber use.

It is technically possible to satisfy projected demand with synthetics, but the rise in world petroleum prices has prompted the rubber industry to look for alternative sources of natural rubber. The principal, if not the only such, source is Guayule. It is conceivable that Guayule eventually could replace Hevea trees because of the susceptibility of the Hevea tree to a number of devastating diseases.

To minimize dependence on dwindling supplies of fossil fuel, attention is being directed to the production of hydrocarbons in plants such as Hevea and Guayule.

Guayule plants thrive on the dry, sandy soil of southwestern U.S. and Mexico. During World War II, extensive plantings of Guayule were carried out in California, near Indio and Salinas. Guayule normally yields one half ton of rubber per acre in cultivation when, after two years, the entire plant is harvested and processed. Various known Hevea tree latex modifiers, such as Etherill (2-ethyl phosphonic acid), which boost latex yield in Hevea trees by preventing clotting of flowing latex will not work with Guayule plants. In Guayule the latex is present as tiny inclusions in the bark, which are not interconnected. The literature suggests that no known plant regulator mechanism was applicable to Guayule, or that if any growth enhancement ever were to be achieved, it would have to come by way of a biochemical modification of the membrane process which produces the polyisoprenic latex.

SUMMARY OF THE INVENTION

The yield of high molecular weight polyisoprene is significantly increased by use of the bioinduction agent according to the present invention. Though the agent does not initiate rubber accumulation, it markedly influences the magnitude of plant response to latex production in the cells. After about a month of growth, plants sprayed with dilute solution of the agent exhibited at least about 20% increase in rubber production, some agents demonstrating increase in yield of up to 400% to 500%.

The bioinduction agents of the invention are selected from amines of the formula:

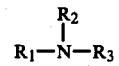

where at least one of $R_1$, $R_2$ and $R_3$ is a hydrocarbon chain containing at least two carbon atoms. $R_1$, $R_2$ and $R_3$ may be hydrogen, alkyl of from 1 to 10 carbon atoms, aryl such as phenyl or $R_1$ may be a carbon-carbon bond and $R_2$ and $R_3$ may be combined into a cyclic structure containing 1 to 10 carbon atoms and hetero atoms such as oxygen, nitrogen, or sulfur such as pyridine, P-ethyl pyridine, 2,4,dichloropyridine or imidazole.

Preferred polyisoprene bioinducing agents of the invention are trialkyl amines of the formula:

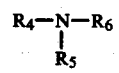

where $R_4$ and $R_5$ are alkyl of 1 to 10 carbon atoms preferably ethyl and at least one of $R_4$, $R_5$ and $R_6$ are substituted with an electron withdrawing group such as halogen, preferably chloro, iodo or bromo, nitro, carbonyl, aldehyde, alkoxy, aryloxy and thio analogs thereof. At least one of $R_4$, $R_5$ and $R_6$ has the structure $-CH_2-(CH_2)_qR_7$ where q is an integer from 1 to 6 and $R_7$ is hydrogen, an electron withdrawing group, aryl such as phenyl, substituted phenl such as $R_9Ph-$ where $R_9$ is alkyl of 1 to 6 carbon atoms or an electron withdrawing group and Ph is phenyl, $(CH_2)_p-O-R_8$ and $(CH_2)_p-S-R_8$ where p is an integer from 1 to 6 and $R_8$ is hydrogen, alkyl of 1 to 4 carbon atoms, aryl such as phenyl or $-Ph-R_9$. $R_4$, $R_5$ or $R_6$ may be substituted with various groups which do not interfere with systemic transport into the plant nor with the bioinduction activity such as phosphoric, sulfuric groups or esters thereof. The compounds can be administered to the plant as the free base, salt, hydroxide or acid addition salt of hydrochloric or phosphoric acid.

Representative compounds are presented in the following table:

| Compounds | |
|---|---|
| 1 | 2-(4-chlorophenylthio) triethylamine hydrochloride (CPTA) |
| 2-6 | $Et_2N(CH_2)_qPh$, where Ph is phenyl and q = 1(2), 2(3), 3(4), 4(5), 5(6) |
| 7-11 | $Et_2NCH_2CH_2OC_6H_4-R_6$ where $C_6H_4$ is phenylene and $R_6$ = H(7), p-Me(8), p-ET(9), p-iso-Pr(10) and p-tert-Bu(11) |
| 12-14 | $Et_2NCH_2CH_2O-C_6H_4OCOR_7$ where $C_6H_4$ is phenylene and $R_7$ is H(12), Me(13) or $C_6H_5$(14) |
| 15 | Choline |
| 16 | N,N-diacetylethanolamine phosphate |
| 17 | 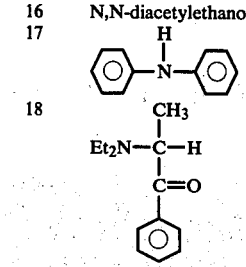 |
| 18 | |

-continued

| Compounds | |
|---|---|
| 19 | 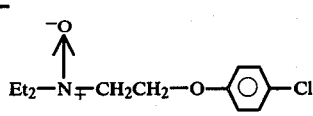 |
| 20 | 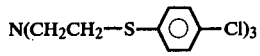 |
| 21 | 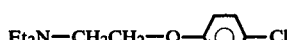 |
| 22-24 | Et₂NCH₂CH₂—O—X 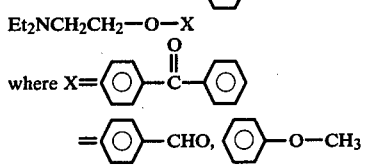 |
| 25 | Et₂N . HCl |
| 26 | Bu₃N . HCl |
| 27 | 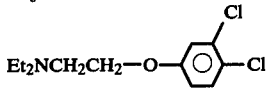 |

The agents of the invention can be applied to the plants in dilute aqueous media by spraying the preparation onto the plant or feeding the preparation to the roots of the plant. 0.1 to 5% of an organic solvent such as alkanol suitably ethanol or isopropanol can be present to assist in dissolving some of the more water insoluble agents. The composition typically contains from 0.05% to 5% by weight of the agent, the remainder being water and optionally a minor amount of from 0.1 to 3% of a surfactant, suitably a nonionic alkylene oxide surfactant such as Tween to assist in penetration of the wax coating on the surface of the plant for topically applied formulations The bioinducers of the invention are generally applicable to increasing the production of polyisoprene having a molecular weight above 300,000 typically about 2,000,000 in plants such as Guayule (*Parthenium argentatum* Gray), Hevea (*Hevea brasiliensis* Muell), *Euphorbia tirucalli* and Russian dandelion (*Taraxacum kox saghz* Rodin).

It is believed that the mechanism responsible for growth enhancement involves a biochemical modification of the membrane process which produces the polyisoprene latex. There is a considerable literature on the biochemical mechanisms of membrane processes. It is known, for example, that lecithin which is a phospholipid or phosphatide which includes the tertiary alkyl amine group, —C₂H₄—N(CH₃)₂, actively participates in membrane-bound enzymatic systems. Similarly, the phosphatide phosphatyl ethanolamine is also membrane active and is a direct analog of the bioinducer structure:

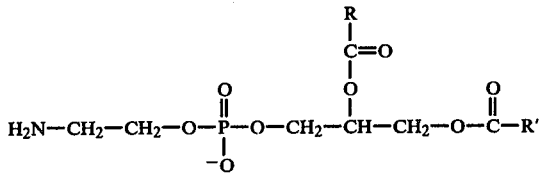

where R and R' are fatty acids and the NH₂ moiety, if substituted with N—(Et)₂ is an analog. It was hypothesized that the formation of polyisoprenic rubber in Guayule occurs through a membrane-bound enzymatic synthesis. Guayule rubber is an isoprene molecule of molecular weight of about 2 million.

A group of compounds of the tertiary alkyl amine type, and particularly triethylamine, have been utilized as citrus color-change regulators by causing an increased production of carotenoid pigments in the citrus by inducing accumulation of lycopene. Lycopene has a low molecular weight polyisoprene structure. It is believed that enhancement of lycopene production in citrus and polyisoprene latex in Guayule proceeds by similar membrane involved mechanisms. This hypothesis was confirmed since it has been demonstrated that the trialkyl amines useful for citrus-color change are also applicable to enhancing production of high molecular weight polyisoprene in Guayule.

In a commercial scheme for production of latex from Guayule, a dilute solution of the agent is sprayed topically on the young plants shortly after planting. Spraying is repeated at regular intervals until the plants are ready for harvest in 2 to 3 years. The plant is readily adaptable to commercial harvesting.

The natural rubber latex in Guayule is found in all parts of the plant except the leaves. It is contained in microscopic cells that are unconnected. The entire plant, except the leaves, must be processed to extract the latex.

Over the years, procedures have been developed that can recover as much as 95% of the available natural rubber. The first step is parboiling, which coagulates the latex in the cells, removes dirt from the roots, and removes the leaves from the stems. Rubber is releasd from the cells by milling in a caustic solution. The milled bagasse sinks to the bottom of the processing vessel. Latex combined with dissolved resins agglomerate into "worms resin" and float to the surface, where they are skimmed off and washed to remove the caustic. The worms contain up to 25% natural resins. Accetone extraction removes the resins and some residual water in a fluid-bed extractor. Acetone is recovered by distillation and the resins are valuable chemical intermediates (such as terpineols) which are recovered separately. The deresinated rubber is then dried and sent on to further processing.

In a gel permeation chromatogram it is all but impossible to distinguish between the molecular weight dispersion of rubber from the Guayule plant and that from the Heavea tree. Similarly, mechanical tests for tackiness, plasticity, and the like show little difference between the two. Tests do show, however, that the amount of curing chemicals needed for processing Guayule rubber into tires is slightly different from that required for Hevea rubber and a modified molding procedure is required.

The production economics of Guayule may be much better than for Hevea. Natural rubber from Hevea trees is extremely labor intensive, but Guayule can probably be harvested mechanically and processed entirely without resorting to hand operations. There also is the probability of some significant by-product credits with Guayule. The natural wax on Guayule leaves can be easily extracted as a clear, white material with a boiling point exceeding that of carnauba wax, which is highly prized and currently sells for more than $2.00 per lb. The bagasse may have some value as a papermaking material. The resins from the Guayule plant have not been fully characterized but appear to contain significant quantities of terpenes similar to those obtained from pine trees. These are used in the paper, paint and essential oils industries.

DESCRIPTION of the Preferred Embodiments

A branch of a Guayule plant was cut, immersed in Hoagland's solution containing about 0.05% CPTA and subjected to light. Growth rate was observed as compared to an adjacent Guayule branch immersed in Hoagland's solution. After about one month, it was found that the control plant for a fixed weight of material yielded 40 mg. of rubber upon extraction, and the treated plant yielded about 59 mg. of rubber; and hence a 50% increase in rubber production occurred in a month.

Rooted young plants of Guayule, about four months old and 10 cm. high, obtained from the Los Angeles County Arboretum were transplanted into a field plot. After allowing the plants to get accustomed to their new enviroment, they were sprayed 13 days later with Mixtures 1 and 2 (see Table 1) and again 30 days later.

Four plants were treated with each mixture, "drenching" all the leaves and stems with a hand sprayer during the warm part of the day, at an ambient temperature of about 70° F. The plants were harvested about 4 weeks after treatment, as described earlier in the text.

TABLE 1

Mixture 1: 1000 ppm N,N-diacetylethanolamine phosphate, 5000 ppm isopropyl alcohol and about 50 ppm of Tween 80 surfactant.

Mixture 2: 1000 ppm of choline phosphate, 5000 ppm isopropyl alcohol and about 50 ppm of Tween 80 surfactant.

The climate during this period was one with occasional heavy rains during which the plants grew vigorously. The plants (four experimental for each compound spray) and controls (four) were harvested and dried at 60° C., ground to a fine powder under liquid nitrogen in a mortar/pestle, and extracted sequentially in a Soxhlet extractor within a microporous Teflon thimble with (a) water, then (b) acetone and finally (c) methylene chloride. The latter contained the rubber which was determined by evaporating a known volumetric aliquot under nitrogen and weighing the residue on a microbalance. The yields are listed in Table 2 in mg. of rubber/gm. dry weight of plant.

TABLE 2

|  | Control | Treated | Gain, % |
|---|---|---|---|
| Mixture 1 | 22.0 | 53.0 | 150 |
| Mixture 2 | 16.5 | 19.4 | 17.6 |

Briefly, the use of N,N-diacetylethanolamine phosphate in the mixture and proportions listed caused an increase in rubber yield, in comparison to that of the control, of about 150%. The choline phosphate was less effective, causing an increase of about 20%.

Lower molecular weight trialkyl amine derivatives such as $(C_2H_5)_2N \cdot CH_2CH_2Br$ appear to provide even higher yields of polyisoprene. Bioinduction of latex of 2 to 6 fold with CPTA as compared to control has been achieved in stem and root tissues of greenhouse grown 4 month old Guayule seedlings and in 8 month old field grown Guayule plants.

It is to be understood that only preferred embodiments of the invention have been described and that numerous substitutions, modifications and alterations are permissible without departing from the spirit and scope of the invention as defined in the following claims.

What is claimed is:

1. A method of stimulating the production of polyisoprene latex having a molecular weight above 300,000 in a Guayule plant comprising the step of:
   administering to the plant an amount effective to increase production of polyisoprene by at least 20% of a bioinducing agent of the formula:

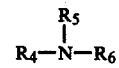

where $R_5$ and $R_6$ are selected from phenyl, $-CH_2(CH_2)_qR_7$ where q is an integer from 1 to 6, $R_7$ is hydrogen; phenyl; an electron withdrawing group; $R_9$ phenyl- where $R_9$ is alkyl of 1 to 6 carbon atoms or an electron withdrawing group; $-(CH_2)_p\text{-}O\text{-}R_8$ or $-(CH_2)_pS-R_8$ where p is an integer from 2 to 6, $R_8$ is hydrogen, alkyl of 1 to 4 carbon atoms, phenyl or phenyl $R_9$, and $R_4$ is hydrogen or $R_5$, and at least one of $R_4$, $R_5$ and $R_6$ has the structure: $-CH_2-(CH_2)_q-R_7$.

2. A method according to claim 1 in which $R_4$ and $R_5$ are ethyl.

3. A method according to claim 1 in which the agent is dispersed in an aqueous carrier.

4. A method according to claim 3 in which the agent dispersion is fed to the roots of the plant.

5. A method according to claim 3 in which the agent dispersion is sprayed onto the plants.

6. A method according to claim 3 in which the agent is present in the dispersion in an amount from 0.05% to 5% by weight.

7. A method according to claim 6 in which the agent dispersion further includes a minor amount of a water-miscible, organic solvent for the agent.

8. A method according to claim 7 in which the dispersion further includes a minor amount of a surfactant.

9. A method according to claim 3 in which the agent is 2-(4-chlorophenylthio) triethyl amine hydrochloride.

10. A method according to claim 1 in which the electron withdrawing group is a halogen.

* * * * *